(12) United States Patent
Frid et al.

(10) Patent No.: US 8,048,139 B2
(45) Date of Patent: Nov. 1, 2011

(54) REVERSIBLE APPLICATOR FOR AN INTRALUMINAL ENDOPROSTHESIS

(75) Inventors: Noureddine Frid, Beersel (BE); Philippe Nicaise, Uccle (BE)

(73) Assignee: Cardiatis, S.A., Isnes (BE)

( * ) Notice: Subject to any disclaimer, the term of this patent is extended or adjusted under 35 U.S.C. 154(b) by 292 days.

(21) Appl. No.: 12/374,848

(22) PCT Filed: Jul. 23, 2007

(86) PCT No.: PCT/EP2007/057563
§ 371 (c)(1),
(2), (4) Date: Feb. 3, 2009

(87) PCT Pub. No.: WO2008/012285
PCT Pub. Date: Jan. 31, 2008

(65) Prior Publication Data
US 2010/0023113 A1 Jan. 28, 2010

(30) Foreign Application Priority Data
Jul. 24, 2006 (EP) .................................. 06117726

(51) Int. Cl.
*A61F 2/06* (2006.01)
(52) U.S. Cl. ...................................................... 623/1.11
(58) Field of Classification Search ............... 623/1.11, 623/1.12, 1.23, 2.11; 606/108, 200, 213
See application file for complete search history.

(56) References Cited

U.S. PATENT DOCUMENTS

| | | | |
|---|---|---|---|
| 3,996,938 A * | 12/1976 | Clark, III | 606/200 |
| 7,524,329 B2 * | 4/2009 | Rucker | 623/1.12 |
| 2002/0120277 A1 | 8/2002 | Hauschild et al. | |
| 2002/0169472 A1 | 11/2002 | Douk et al. | |
| 2004/0015224 A1* | 1/2004 | Armstrong et al. | 623/1.12 |
| 2004/0181237 A1 | 9/2004 | Forde et al. | |
| 2006/0155305 A1 | 7/2006 | Freudenthal et al. | |

FOREIGN PATENT DOCUMENTS

| | | |
|---|---|---|
| CA | 2213291 | 2/1998 |
| EP | 0829242 | 3/1998 |
| WO | WO 99/42059 | 8/1999 |
| WO | WO 99/47075 | 9/1999 |
| WO | WO 2005/027751 | 3/2005 |

OTHER PUBLICATIONS

International Search Report for International Application No. PCT/EP2007/057563, 3 pages.

* cited by examiner

*Primary Examiner* — Melanie Tyson
(74) *Attorney, Agent, or Firm* — Barnes & Thornburg LLP

(57) ABSTRACT

A reversible applicator for an intraluminal endoprosthesis with a pusher, an outer sheath sliding longitudinally relative to this pusher, and an endoprosthesis arranged at it's distal part. A retention element formed by an expandable braid that widens in a bulb shape in the expanded state, integrally joined to the pusher, is arranged longitudinally inside the endoprosthesis that is to be fitted in place. This bulb compresses the proximal part of the endoprosthesis against an inner wall of the sheath in such a way as to allow the endoprosthesis to be retracted inside the sheath.

12 Claims, 4 Drawing Sheets

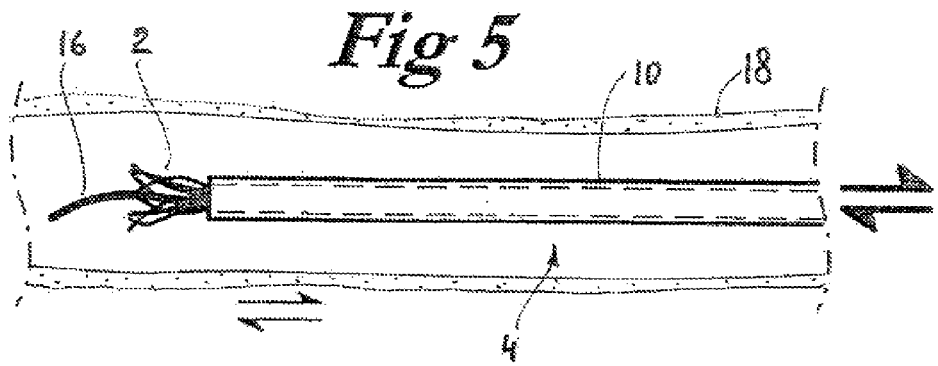
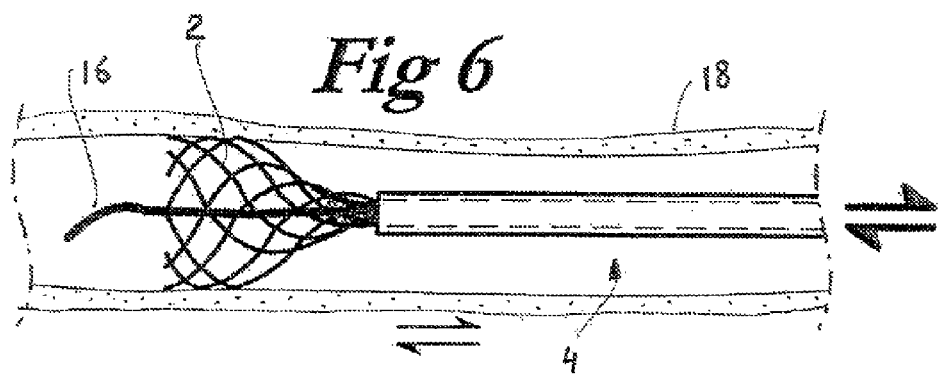
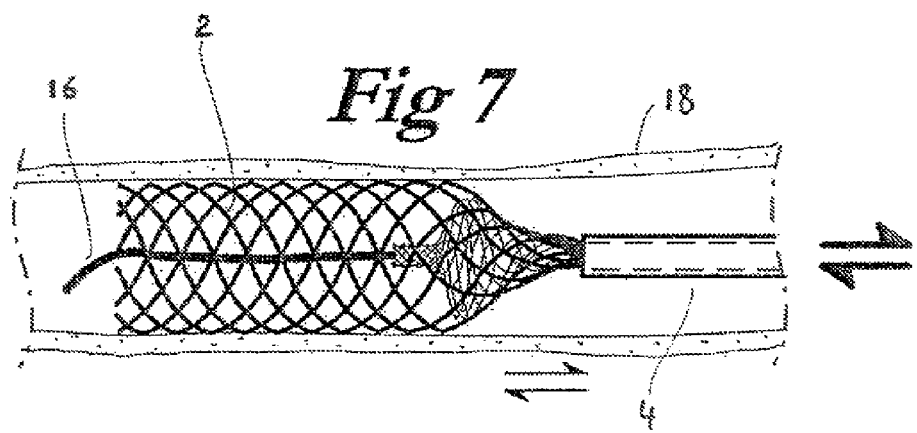

REVERSIBLE APPLICATOR FOR AN INTRALUMINAL ENDOPROSTHESIS

CROSS-REFERENCE TO RELATED APPLICATION

This application is a National Stage filing of PCT International Application Serial No. PCT/EP2007/057563, filed Jul. 23, 2007, which claims the benefit of European Patent Application Serial No. 06117726.7, filed Jul. 24, 2006, the disclosures each of which are expressly incorporated herein by reference.

FIELD OF THE INVENTION

The invention relates to devices for placement of intraluminal endoprostheses, such as stents, and permits possible repositioning of these endoprostheses. The invention applies particularly to self-expanding endoprostheses.

BACKGROUND OF THE INVENTION

When fitting an intraluminal endoprosthesis in place, the operator depends entirely on medical imaging. The small dimensions of the endoprostheses and the low contrast of the images mean that it is very difficult, even for an experienced operator, to guarantee 100% correct positioning. This is particularly true of self-expanding endoprostheses, which have a tendency to deploy completely when they emerge from the applicator and which it is difficult, if not impossible, to reposition.

Numerous applicators are known that are supposed to permit retraction and subsequent repositioning.

U.S. Pat. No. 5,026,377 discloses an applicator for a self-expanding stent. The proximal end of the stent is fixed to a central pusher by an adhesive or by the presence of a bead placed on this pusher. U.S. Pat. No. 5,628,755 and U.S. Pat. No. 5,246,421 describe applicators for plastically deformable stents (balloon stents). In U.S. Pat. No. 5,628,755, a sheath allows the length of the balloon to be adapted to stents of different lengths.

WO 96/13228 discloses an applicator equipped with a malleable core placed on the pusher for holding an endoprosthesis in place until it has been completely released.

WO 99/47075 describes a reversible applicator for an endoprosthesis, comprising an internal balloon that ensures that the applicator engages on the endoprosthesis until it has completely emerged from its housing.

In practice, none of these applicators gives 100% reliable results: once quite a limited length of the stent has been released, it is impossible to reverse it in order to correct its position. All these devices are also quite bulky because of the presence of the retention device inside the sheath, which fact automatically places a limit on the diameter of the vessels in which they can be employed.

EP-829 242 describes a catheter for removing an expanding endoprosthesis already implanted in a duct. The transport catheter comprises and outer tube and an axially moving inner tube. The inner tube bears hooks at its free end. When it is pushed outwardly, the hooks extend out of the catheter tube and spread, gripping the prosthesis so that it can theoretically be compressed and pulled into the catheter.

US 2004/0181237 relates to medical devices for manipulating medical implants such as, for example, stents, distal protection filters, and septal occluders in a patient's body, and the methods of use thereof. This medical device includes a sleeve and an expandable component joined to the sleeve which transitions between a collapsed configuration and a deployed configuration for capturing a medical implant in a patient's body.

In fact, it has proven practically impossible to remove a luminal endoprosthesis once it has been left in close contact with the wall of a vessel.

It has thus been sought to develop an applicator which takes up minimal space, that is to say occupies a small diameter when folded up, and which permits reversal of the positioning of an endoprosthesis until an advanced stage of the deployment procedure.

SUMMARY OF THE INVENTION

The subject of the invention is a reversible applicator for an intraluminal endoprosthesis, comprising: a distal part and a proximal part, a pusher, and an outer sheath sliding longitudinally relative to this pusher. A retention element composed of an expandable braid that widens in a bulb shape in the expanded state, integrally joined to the pusher, is arranged longitudinally inside the endoprosthesis that is to be fitted in place. The proximal part of the endoprosthesis is pinched between the deployed bulb and the inner wall of the sheath, thus allowing the endoprosthesis to be retracted inside the sheath as long as the proximal end of the endoprosthesis has not passed beyond the distal end of the sheath.

According to an advantageous embodiment, the endoprosthesis comprises a self-expanding framework.

According to another advantageous embodiment, the endoprosthesis comprises a plastically deformable framework.

According to a preferred embodiment, the braid is made of a metal chosen from among the alloys of nickel, the alloys of titanium, or nitinol.

According to a preferred embodiment, the distal end of the bulb is closed by an area of crimping. This area of crimping can advantageously comprise a radiopaque marker.

The area of crimping preferably has an orifice extending through it to permit passage of a guide.

If the endoprosthesis comprises a braided framework, the braid forming the bulb is preferably composed of a number of filaments corresponding to that of the endoprosthesis. In this case too, the filaments of the braid forming the bulb advantageously have a diameter substantially equal to that of the filaments forming the endoprosthesis.

According to an advantageous embodiment, the distal part of the bulb, in the deployed state, is drawn back inside the proximal part of said bulb along all or part of its length, in order to double the wall of said bulb.

An advantage of the invention is that the endoprosthesis can be retained by the applicator and recaptured even after 90% of its length has been deployed.

Another advantage is the ease with which the endoprosthesis and the retention element can be placed in the applicator.

Another advantage lies in the very small dimensions (diameter) of the applicator which is thus equipped and which can consequently be introduced into vessels of very small diameter (especially for interventions in the cervical region).

BRIEF DESCRIPTION OF THE DRAWINGS

These and other aspects of the invention will become clear from the detailed description of particular embodiments of the invention, reference being made to the attached drawings, in which:

FIGS. 5 to 10 are schematic cut-away side views of different steps involved in the placement of the endoprosthesis from FIGS. 1 to 4.

The figures are not drawn to scale.

Generally, similar elements are designated by similar references in the figures.

DETAILED DESCRIPTION OF THE FIGURES

FIGS. 1 to 4 show the different steps involved in fitting an endoprosthesis 2 (shown here in the form of a stent) in the applicator 4 according to the invention. Only the distal end part 6 of the applicator 4 is shown.

Figure 1:
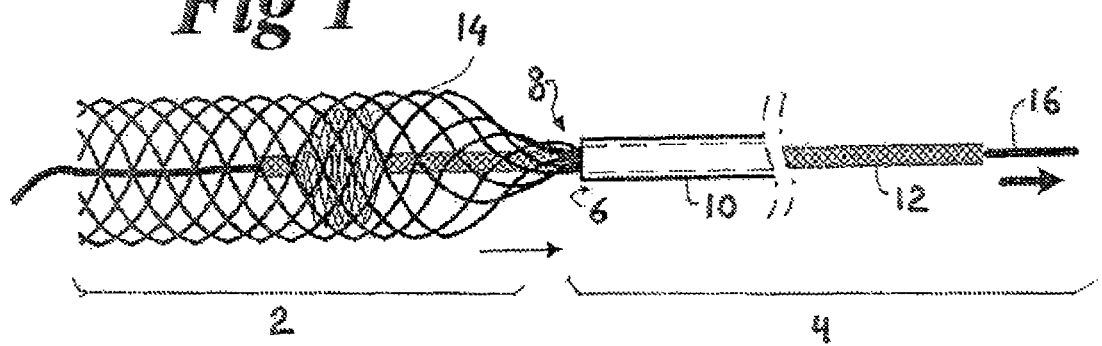
FIGS. 1 to 4 are schematic cut-away side views of different steps involved in introducing an endoprosthesis with the applicator according to the invention.

In FIG. 1, the proximal part 8 of the endoprosthesis 2 is compressed and introduced into the distal end 6 of an outer sheath 10 that surrounds the applicator 4.

A retention element 12, formed by a braided framework continued inside the sheath 10 by a pusher 13, is arranged inside the endoprosthesis 2.

Near the distal end of this retention element, the framework comprises a bulb-shaped widening 14, which is clearly visible in the deployed state (see FIGS. 11 to 14). The applicator and the various elements described above slide along a guide wire 16 designed to bring the end of the applicator to the site of release of the endoprosthesis.

Figure 2:
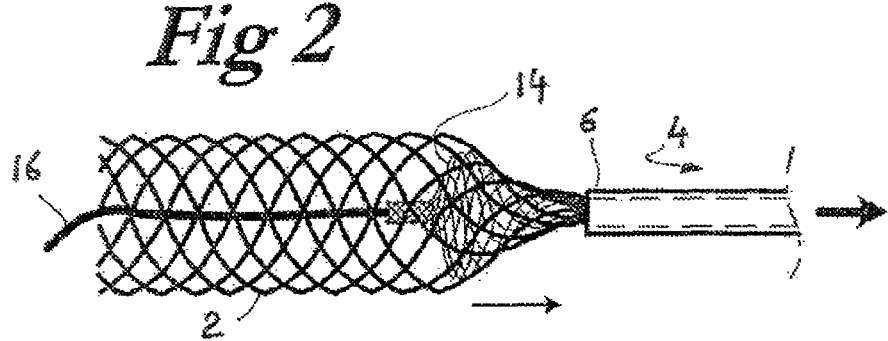

FIG. 2 shows what happens when a traction is exerted on the retention element from the direction of the proximal part of the applicator 4. The bulb-shaped widening 14 comes to rest against the proximal <<funnel-shaped>> part of the endoprosthesis 2. The radial force resulting from the compression of the bulb 14 generates a frictional force against the inner wall of the endoprosthesis 2. The various parameters governing this frictional force are calculated such that the bulb causes the endoprosthesis 2 and the force to penetrate the sheath 10 by adopting a contracted shape.

Figure 3:
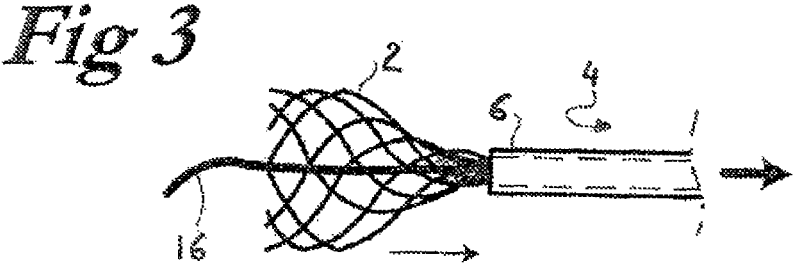
Figure 4:
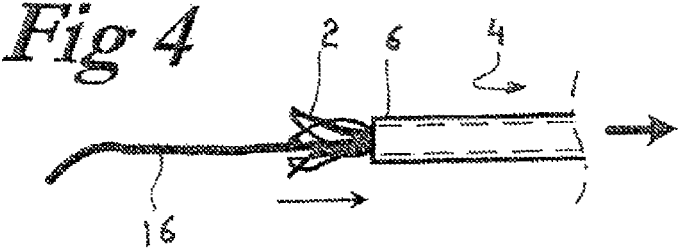

The retention element 12 and the endoprosthesis 2 gradually move farther inside the sheath (FIGS. 2 and 3).

With the retention element 12 composed of a braid, the strands forming this braid align themselves inside the sheath 10 in the compressed state, such that this element finally takes up an insignificant amount of space inside the sheath 10. The diameter of the applicator can therefore be substantially reduced compared to other retrieval devices, with the result that the applicator can be introduced without difficulty into extremely fine blood vessels and can thus serve in particular for cervical applications.

FIGS. 5 to 10 show the different steps involved in the in situ release of an endoprosthesis inside a blood vessel 18 that is to be treated.

In FIG. 5, the applicator 4, which the operator has slid along the guide wire 16 from an introduction site, has arrived at the site that is to be treated.

The operator, while keeping the endoprosthesis 2 in place using the pusher 13, exerts a traction on the sheath 10: the endoprosthesis 2 begins to emerge from the distal end 6 of the sheath 10. As is shown in FIG. 6, the endoprosthesis 2 (which in this case is a self-expanding stent) begins to deploy. Its side wall comes to rest against the side wall of the blood vessel 18 in such a way as to restore the desired diameter to the latter. As the operator continues to pull on the sheath 10, the bulb 14 of the retention element 12 begins to emerge from the sheath 10.

Up to this stage, the operator has the possibility of interrupting the placement procedure at any moment.

If, in light of the information provided to him by medical imaging (X-rays, scanner, etc.), he feels that the position of the endoprosthesis 2 is not ideal, all he has to do is reverse the movement of the sheath 10. The endoprosthesis 2, still maintained by friction via the retention element 12, resumes its contracted shape and arrives back inside the sheath without damaging the wall of the blood vessel, according to the (reverse) sequence of FIGS. 7-6-5.

The difficulty involved in positioning an endoprosthesis 2 is the result of a number of factors. On the one hand, in the case of an endoprosthesis with a braided framework, the type of meshing and the angle of intersection of the filaments will mean that the coefficient of elongation of the endoprosthesis 2 may vary greatly during the change from the contracted state to the deployed state. On the other hand, the presence of secondary vessels linked to the treated vessel may seriously complicate the operator's task. This is because some types of endoprostheses 2 risk occluding the point of entry of these secondary vessels into the treated vessel, with adverse consequences on the irrigation of the tissues situated downstream of these vessels.

Depending on the time available to him, the operator may therefore have to make several attempts before determining the most suitable position.

Figure 8:
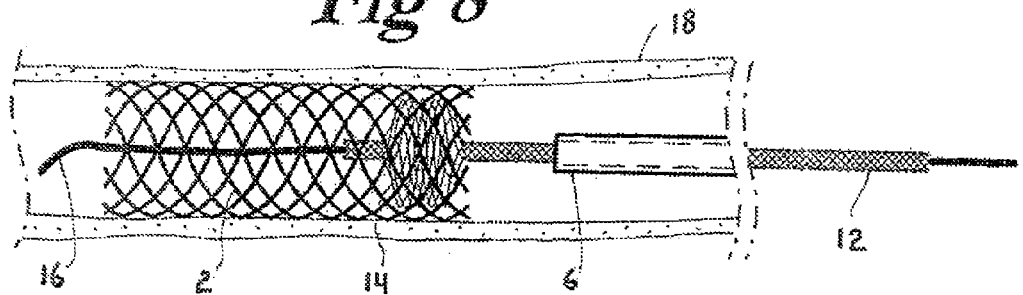
Figure 9:
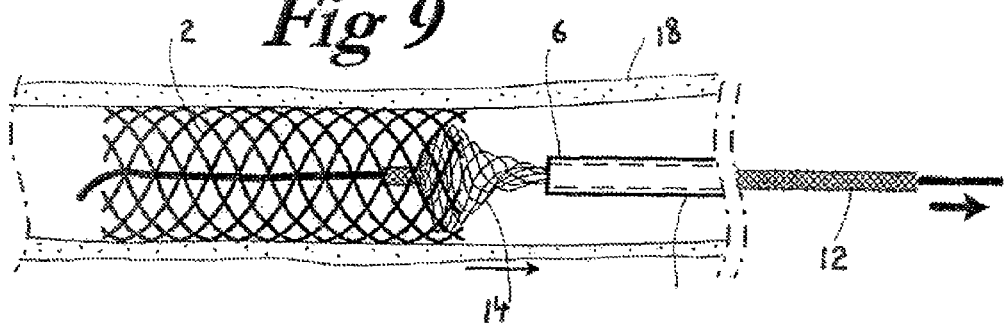
Figure 10:
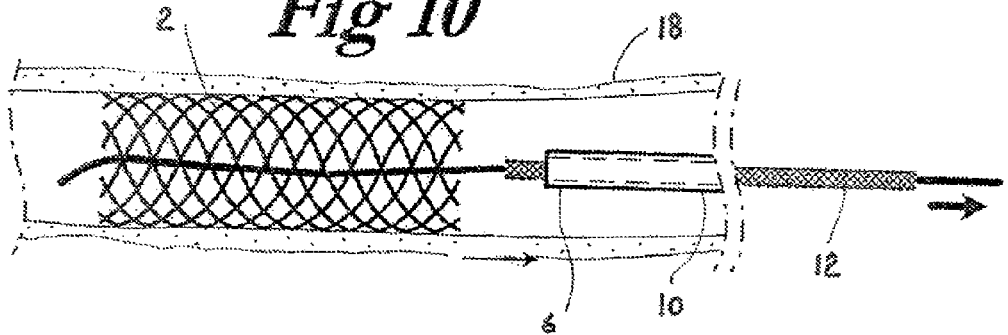

Once the operator feels the appropriate site has been reached, at the stage shown in FIG. 7 (which corresponds to between 90 and 95% of the length of the endoprosthesis), he is able to complete the deployment process. As is shown in FIG. 8, the sheath 10 is pulled back sufficiently to disengage the proximal part of the endoprosthesis, which, now completely freed, deploys integrally along the wall of the blood vessel 18. A combined movement of the pusher and/or of the sheath 10 is all it takes to bring the bulb 14 of the retention element back inside the sheath 10 (FIG. 9), and the applicator can be withdrawn without difficulty (FIG. 10).

Although the applicator has been described here in the context of the placement of a self-expanding endoprosthesis (or of a stent), it goes without saying that it can also be used for placement of an endoprosthesis with a plastically deformable framework (<<balloon>> endoprosthesis).

Figure 13:
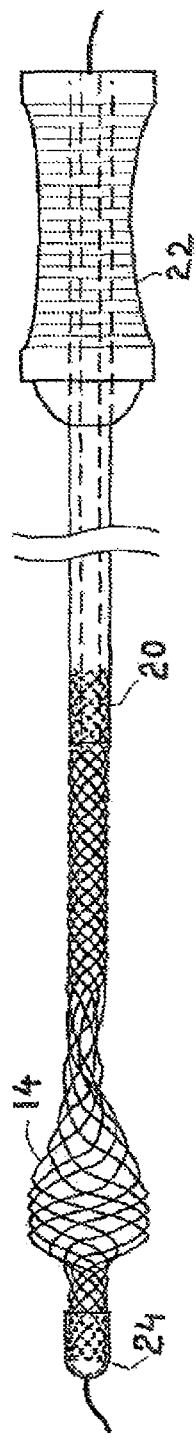
Figure 14:
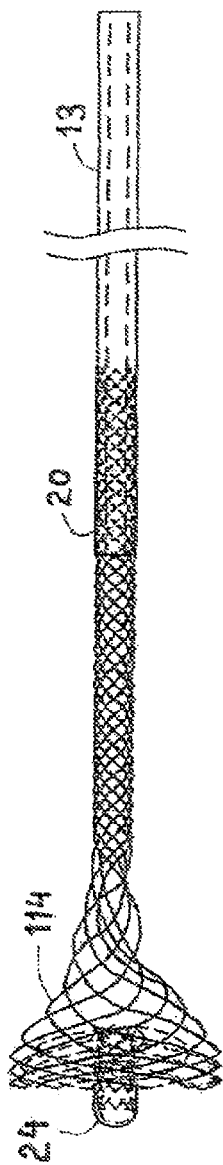

The applicator according to the invention is distinguished by its small diameter and also by the extreme ease with which it is manipulated. Nor is it necessary to use complicated control means (compressed air, etc.) to activate it. Its design is also very simple since the <<mechanical>> parameters (such as the frictional force generated) to be complied with have been determined for different types of endoprosthesis. In particular, the pusher 13 and the retention element 12 can be joined together by fusion or adhesive bonding 20, as is shown in FIGS. 13 to 14. To make manipulation easier, the proximal end of the pusher is generally terminated by a grip element (handle 22).

FIGS. 11 to 14 show various possible, but non-limiting embodiments of the retention bulb 14.

Figure 11:
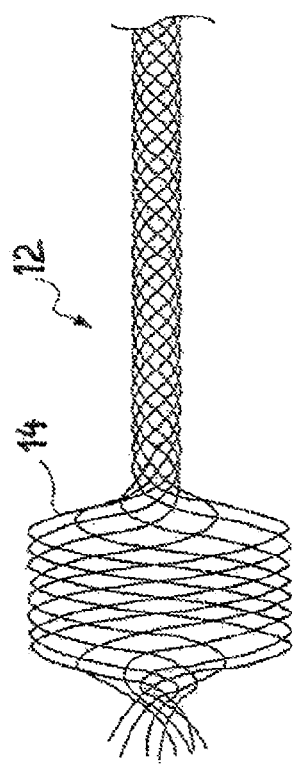
FIGS. 11 to 14 are schematic cut-away side views of different embodiments of the retention element of the applicator according to the invention.

In FIG. 11, the bulb 14 is terminated at its distal end by simple tightening, the strands being left free. This embodiment has the advantage of taking up a minimum amount of space. However, it has a lesser degree of precision.

Figure 12:
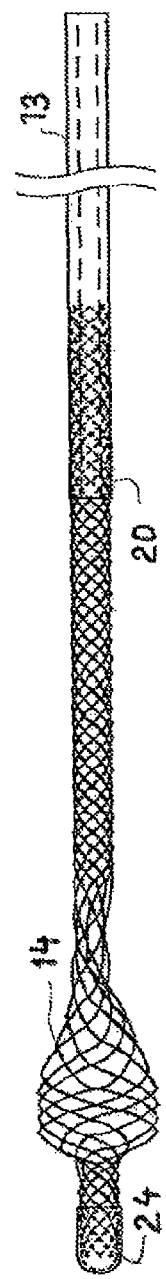

The bulb in FIG. 12 is closed at its distal end by an area of crimping 24, which permits more precise calibration of the radial force generated and thus a recapture of the endoprosthesis at a very advanced stage of the deployment. This embodiment has another advantage too: the low mass of the endoprosthesis 2 normally makes it very difficult to locate by medical imaging, all the more so if operating in the cervical region, inside the skull. However, the operator may be helped in his decision by the presence of radiopaque markers that show him more precisely the position of the endoprosthesis and/or of the end of the applicator in the body. To help him in this task, a marker of radiopaque material (platinum, gold, titanium) can be placed on the area of crimping that closes the bulb. Moreover, the material used for the crimping can itself be radiopaque.

As is shown in FIG. 13, the area of crimping 24 generally has a hole extending through it to permit passage of a guide wire 16.

The embodiment of the bulb 114 in FIG. 14 has another particularity: it is partially turned back in a corolla shape at the distal end, which increases its radial force, all other things being equal (number, nature and diameter of the filaments). It is also possible to <<double>> the bulb over all or part of its length by forcing the area of crimping farther forwards into the bulb at the moment it is shaped. It will be noted that, even when <<doubled>> in this way, the bulb does not take up more room in the outer sheath, given that it is completely drawn out at the moment of insertion into this sheath.

As has been mentioned above, the parameters relating to the bulb must be well adapted to the mechanical characteristics of the endoprosthesis 2 that is to be fitted in place. If the framework of the endoprosthesis is formed by braiding, a decisive factor for these mechanical characteristics is the braiding itself: its <<pitch>> and the number, nature and diameter of the filaments. Consequently, tests show that it is particularly advantageous to use for the retention element a braid whose characteristics are as close as possible to those of the endoprosthesis that is to be fitted in place, especially as regards the number or even the diameter of the filaments. For the filaments of the bulb, however, it is possible to go down to a diameter corresponding to only 80% of that of the filaments of the endoprosthesis, which allows space to be saved and consequently permits a reduction in the diameter of the applicator (and, as an indirect consequence, the possibility of treating blood vessels of still smaller diameter). It goes without saying that the various criteria can be combined, or other criteria can be applied, to obtain an equivalent retention effect, for example the roughness or surface condition of the filaments, the <<doubling>> of the bulb, etc.

Moreover, the relative diameter of the bulb also plays a role in the pressure that is applied to the wall of the endoprosthesis in order to maintain it in place. Tests show that an optimal result is achieved when the diameter of the bulb is between 90 and 95% of the internal diameter of the endoprosthesis. Beyond 95%, the friction risks becoming too great, whereas below 90% there is a risk of the contact being insufficient for successful retraction.

It will be obvious to a person skilled in the art that the present invention is not limited to the examples illustrated and described above. The invention includes each of the novel features and also their combination. The presence of reference numbers cannot be considered as implying a limitation. The use of the term <<comprises>> cannot in any way be taken to exclude the presence of further elements other than those mentioned. The use of the indefinite article to introduce an element does not exclude the presence of a plurality of these elements. The present invention has been described in relation to specific embodiments that have a purely illustrative value and must not be considered as limiting the invention.

The invention claimed is:

1. A reversible applicator, for an intraluminal endoprosthesis at least partially disposed within the reversible applicator, comprising:

an outer sheath having a distal end and a proximal end;

a pusher, the outer sheath sliding longitudinally relative to the pusher;

a retention element having a proximal portion and a distal portion and being disposed at least partially and longitudinally within an intraluminal endoprosthesis, the retention element comprising an expandable braid and integrally joined to the pusher, wherein, when the intraluminal endoprosthesis begins to deploy from the outer sheath the distal portion of the retention element also deploys from the outer sheath, thereby forming a bulb with a portion of the retention element, the bulb disposed within the intraluminal endoprosthesis causing a portion of the intraluminal endoprosthesis to be pinched between said bulb and an inner wall of the distal end of the outer sheath such that the intraluminal endoprosthesis is capable of being retracted inside the outer sheath as long a portion of the endoprosthesis remains disposed within the distal end of the outer sheath.

2. The reversible applicator according to claim 1, wherein the intraluminal endoprosthesis comprises a self-expanding framework.

3. The reversible applicator according to claim 1, wherein the intraluminal endoprosthesis comprises a plastically deformable framework.

4. The reversible applicator according to claim 1 wherein the expandable braid comprises a metal selected from the group of an alloy of nickel, an alloy of titanium, and nitinol.

5. The reversible applicator according to claim 1 wherein the distal portion of the retention element deployed from the outer sheath further comprises an area of crimping, the area of crimping disposed distal to the bulb.

6. The reversible applicator according to claim 5, wherein the area of crimping comprises a radiopaque marker.

7. The reversible applicator according to claim 6, wherein the area of crimping has an orifice extending through it to permit passage of a guide.

8. The reversible applicator according to claim 1 wherein the area of crimping has an orifice extending through it to permit passage of a guide.

9. The reversible applicator according to claim 8 wherein the intraluminal endoprosthesis comprises a braided framework including of a plurality of filaments, the expandable braid of the retention element including a plurality of filaments, said plurality of the filaments of the expandable braid corresponding to said plurality of the filaments of the braided framework of the intraluminal endoprosthesis.

10. The reversible applicator according to claim 1 wherein the intraluminal endoprosthesis comprises a braided framework including a plurality of filaments, the expandable braid of the retention element including a plurality of filaments, said plurality of the filaments of the expandable braid corresponding to said plurality of the filaments of the braided framework of the intraluminal endoprosthesis.

11. The reversible applicator according to claim 10, wherein the plurality of filaments of the expandable braid of the retention element have a diameter substantially equal to the plurality of the filaments of the braided framework of the intraluminal endoprosthesis.

12. The reversible applicator according to claim 1 wherein a distal portion of the expandable braid of the retention element in the deployed state, is retracted back inside at least a portion of said bulb.

* * * * *